United States Patent [19]

Hugues et al.

[11] Patent Number: 5,264,645

[45] Date of Patent: Nov. 23, 1993

[54] PROCESS AND APPARATUS FOR THE CATALYTIC CONVERSION OF A CHARGE CONTAINING AN OXYGEN COMPOUND COMPRISING THE QUENCHING AND SIMULTANEOUS SEPARATION OF THE PRODUCTS FORMED AND THE CATALYST

[75] Inventors: François Hugues, Vernaison; Jean P. Burzynski, Sainte Foy Les Lyon; Daniel Vuillemot, Saint Genis Laval; Pierre Galtier, Vienne; Thierry Gauthier, Saint Genis Laval, all of France

[73] Assignee: Institut Francais Du Petrole, Rueil Malmaison, France

[21] Appl. No.: 848,599

[22] Filed: Mar. 9, 1992

[30] Foreign Application Priority Data

Mar. 7, 1991 [FR] France ................... 91 02892

[51] Int. Cl.⁵ ............................... C07C 1/24
[52] U.S. Cl. .................... 585/640; 585/635; 585/639; 585/921
[58] Field of Search ........... 585/639, 640, 635, 921; 422/147

[56] References Cited

U.S. PATENT DOCUMENTS

| | | | |
|---|---|---|---|
| 4,197,418 | 4/1980 | Lee et al. | 585/469 |
| 4,229,608 | 10/1980 | Chen et al. | 585/640 |
| 4,423,274 | 12/1983 | Daviduk et al. | 585/640 |
| 4,627,911 | 12/1986 | Chen et al. | 585/640 |
| 4,686,313 | 8/1987 | Bell et al. | 585/327 |

Primary Examiner—Anthony McFarlane
Attorney, Agent, or Firm—Millen, White, Zelano, & Branigan

[57] ABSTRACT

The conversion of a charge comprising at least one oxygen compound is performed in a reactor C, into which the charge is introduced by the pipe (11), the solid catalytic particles forming the dense phase D1 by the pipe (14) and the solid entrainment gas by the pipe (12). The reactor is connected by a pipe (1) to a cocurrent cyclone separator-mixer (MS) making it possible to separate a solid phase from a gaseous phase containing the conversion products recovered by the pipe (4'), while carrying out a quenching of said gaseous phase by a product M2 introduced by the pipe (3). The phase D1 is fed by the pipe (7) to a regenerator R before being returned by the pipe (13) into the reactor C. The mixture of the gaseous phase and the product M2 is separated in a separator and the product M2, optionally after cooling, is recycled to the mixer-separator (MS).

11 Claims, 3 Drawing Sheets

PROCESS AND APPARATUS FOR THE CATALYTIC CONVERSION OF A CHARGE CONTAINING AN OXYGEN COMPOUND COMPRISING THE QUENCHING AND SIMULTANEOUS SEPARATION OF THE PRODUCTS FORMED AND THE CATALYST

SUMMARY OF THE INVENTION

The invention relates to an entrained bed catalytic conversion process for a charge comprising at least one oxygen compound and more particularly at least one alcohol such as methanol and at least one ether-oxide such as dimethyl ether, as well as an apparatus for performing this process and comprising at least one cocurrent cyclone separator-mixer permitting the very fast separation of the solid particles and the gases and the quenching of said gases.

This process more particularly applies to the production of olefinic hydrocarbons, particularly for petrochemical uses and which process employs compounds having 2 to 4 carbon atoms in a molecule, in the presence of a catalyst such as a zeolite circulating in an entrained bed reactor. A particular use referred to in exemplified manner here is the catalytic conversion of methanol into ethylene and/or propylene-rich hydrocarbons. The prior art is e.g. illustrated by U.S. Pat. No. 4,197,418.

One of the essential factors in the selective production of light olefins and more particularly ethylene and/or propylene by the conversion of methanol is the control of the contact time between the charge and the catalyst. This contact between the charge and the catalyst must be both short and uniform (or regular) in time, which imposes a speed and uniformity of the contacting between the catalyst grains and the liquid or gaseous charge. It is therefore important to more particularly control the charge quantity introduced in conjunction with the catalyst quantity with which it comes into contact and to keep constant the contact time between the charge and the catalyst, so as to obtain the optimum selectivity therefore the desired ethylene compound or compounds. In the absence of such control the tendency of the reaction is to lead to a wide range of saturated and unsaturated hydrocarbons generally extending from methane to hydrocarbons having up to 10 carbon atoms in a molecule or more, such as those conventionally constituting a naphtha fraction.

In the methanol conversion processes using the entrained bed process described in the prior art, there is frequently an insistence on the importance of the optimization and control of the contact time between the catalytic particles and the charge. As is e.g. stated in U.S. Pat. No. 4,229,608, this contact time must be relatively short. However, no mention is made of the use of a separation and quenching system permitting an effective, fast separation of the solid particles and the gases containing the products of the reaction and the fast quenching of said gases.

The association of well chosen operating conditions, an ultra-fast separation of the catalytic particles and the gaseous products including the products of the conversion and a fast and effective quenching of these gaseous products makes it possible to avoid a subsequent evolution towards higher molecular weight products, while simultaneously significantly improving the selectivity with respect to the desired ethylene compound or compounds, which was not the case in the prior art, such as is e.g. described in U.S. Pat. No. 4,229,608.

More specifically, the present invention relates to a process for the catalytic conversion of a charge comprising at least one oxygen compound, into olefinic hydrocarbons rich in compounds having 2 to 4 carbon atoms in a molecule and comprising the entrained bed conversion of said charge, in an elongated conversion reaction zone, under appropriate conditions and in the presence of a catalyst in the form of solid particles, said process including:

a) a supply stage to a zone in the vicinity of a first end of said reaction zone of at least one dense phase D1 in the form of solid particles containing catalytic particles, b) a supply stage, in a zone located in the vicinity of a first end of said reaction zone of at least one entrainment fluid, c) a supply stage for the charge and, in the case of an at least partly liquid charge, the atomization of said charge downstream, in the solid particle displacement direction, with respect to the supply stage of said solid particles, d) a stage of contacting said solid particles and said charge in a zone located in the vicinity of the first end.

e) a stage of circulating the solid particles and the charge in the conversion zone during which the conversion of said charge takes place and the catalytic solid particles are at least partly deactivated by the deposition of coke thereon, f) a separation stage, wherein from a mixture M1, the dense phase D1 and the resultant of gases, a light phase L1, containing the products of the at least partial conversion of said charge in a separation and quenching zone located in the vicinity of a second end of the conversion zone opposite to said first end, g) a stage of regenerating, in at least one regenerating zone, at least part of the solid catalytic particles contained in the dense phase D1 and which are at least partly deactivated and h) a stage of recycling said dense phase D1 containing the solid catalytic particles in an at least partly regenerated form, into a recycling zone in the vicinity of said first end, characterized in that during stage f), the dense phase D1 is separated from the light phase L1 containing the conversion products and said light phase is quenched in a separation and quenching zone incorporating in combination:

at least one external enclosure, extended along at least one axis, having a substantially circular cross-section of diameter (Dc) and length (L), into which is introduced in the vicinity of a first end of said external enclosure by an intake (1), called the external intake, the mixture M1 which is circulated from said first end to a second end opposite to the first end of said external enclosure, while giving at least to the phase L1 of said mixture a helical movement in the flow direction of said mixture M1, the dense phase D1 is separated from the light phase L1, by means of an outlet (7), called the external outlet, recovery takes place of at least part of the dense phase D1 in the vicinity of said second end and the light phase L1 is passed into the intake (4), called the second internal intake, of the second internal enclosure described hereinafter.

at least one first internal enclosure, extended along at least one axis and having a substantially circular cross-section, which has a length (Li) smaller than (L) and arranged coaxially relative to said external enclosure, into which is introduced by an intake (3), called the first internal intake, in the vicinity of the external intake of the external enclosure, a light phase L2 or a dense mixture D2 or a mixture M2 comprising both the light phase L2 and a dense phase D2, said phases L2 or D2 or said mixture M2 having a temperature below the temperature of the phase L1, in the same direction as the mixture M1, the phases L2 or D2 or said mixture M2 is circulated from said first internal intake to a first internal outlet (3'), which has an internal diameter (Di) smaller than (Dc), which is opposite to said first internal intake (3), by which the phase L2 or the phase D2 or the said mixture M2 leaves said first internal enclosure by said outlet (3').

at least one second internal enclosure extended along at least one axis having a substantially circular cross-section and positioned coaxially relative to said first internal enclosure, comprising a first end located at a distance (Le) from the first internal outlet (3') of the first internal enclosure, said distance (Le) being such that the sum of the distances (Le) and (Li) is at the most equal to (L) and into which penetrates, by an intake (4) called the second internal intake and having an internal diameter (De) equal to or larger than (Di) and smaller than (Dc), at least part of the light phase L1 and at least part of the light phase L2 or the dense phase D2 or the mixture M2, and from said second enclosure is discharged by a second internal outlet (4'), which is opposite to said second internal intake, a mixture M3 comprising at least part of the light phase L1 and at least part of the light phase L2 or the dense phase D2 or the mixture M2 and the mixture M3 is passed into a zone in which separation and recovery takes place on the one hand of said phase L2 or said phase D2 or said mixture M2 and on the other hand the cooled phase L1 containing the olefinic hydrocarbons formed during the conversion.

In a preferred embodiment of the process according to the invention, the distance (Le) between the first internal outlet (3') of the first internal enclosure and the first internal intake (4) of the second internal enclosure is approximately 0.1×(Dc) to approximately 10×(Dc).

In a preferred embodiment of the process according to the invention, the mixture M1 is introduced into the separation and quenching zone in a direction substantially perpendicular to the axis of its external enclosure or in a direction substantially parallel to the axis of said external enclosure.

In an embodiment of the process according to the invention introduction takes place, e.g. via at least one introduction means, into the separation and quenching zone of at least one fluid (L3) making it possible to simultaneously carry out the stripping of the solid particles of the dense phase D1. This fluid is normally a gas chosen from among the gases conventionally used for carrying out such a stripping operation. This gas will e.g. be steam or an inert gas, such as e.g. nitrogen.

In the process of the present invention, the separation of the dense phase D1 and the quenching of the light phase L1 are performed in a single apparatus referred to hereinafter either as the cocurrent cyclone separator-mixer, or the apparatus.

Unlike in the case of the apparatuses used in the prior art for carrying out separation and in particular where the apparatus used for performing the separation is a reverse cyclone separator, this type of apparatus makes it possible by placing the internal intake for the light phase L1 (which is essentially gaseous) relatively close to the intake (at a distance less than the length (Lc) of the reverse separator) for the mixture M1 (containing the solid particles forming a dense phase D1 and the gases forming a light phase L1) and by controlling the circulation of the light phase in the internal intake and the flow in the intake of the mixture M1, to obtain a rapid separation of the phases, while still maintaining a good efficiency of the collection of the dense phase D1 and while having an acceptable light phase residence time distribution. Moreover, the apparatus used in the invention makes it possible to limit the time during which the gases, separated from the hot solids, remain at a relatively high temperature. This leads to a maximum limitation of the secondary thermal reactions of the olefins formed during the conversion. Apart from the simplification of the equipment necessary for the separation and the quenching, the apparatus used in the process of the invention permits a very effective, ultrafast quenching of the gaseous products.

BRIEF DESCRIPTION OF THE DRAWINGS

The invention will be better understood from the following description of a number of embodiments given in an illustrative and non-limitative manner, with reference to FIGS. 1, 2A, 2B, 3 and 4, where similar members are designated by the same reference letters and numerals.

In FIG. 3 the size of said means (6), in the direction perpendicular to the axis of the external enclosure, is smaller than the size of the external outlet (5).

DETAILED DESCRIPTION OF THE DRAWINGS

Figure 2A:
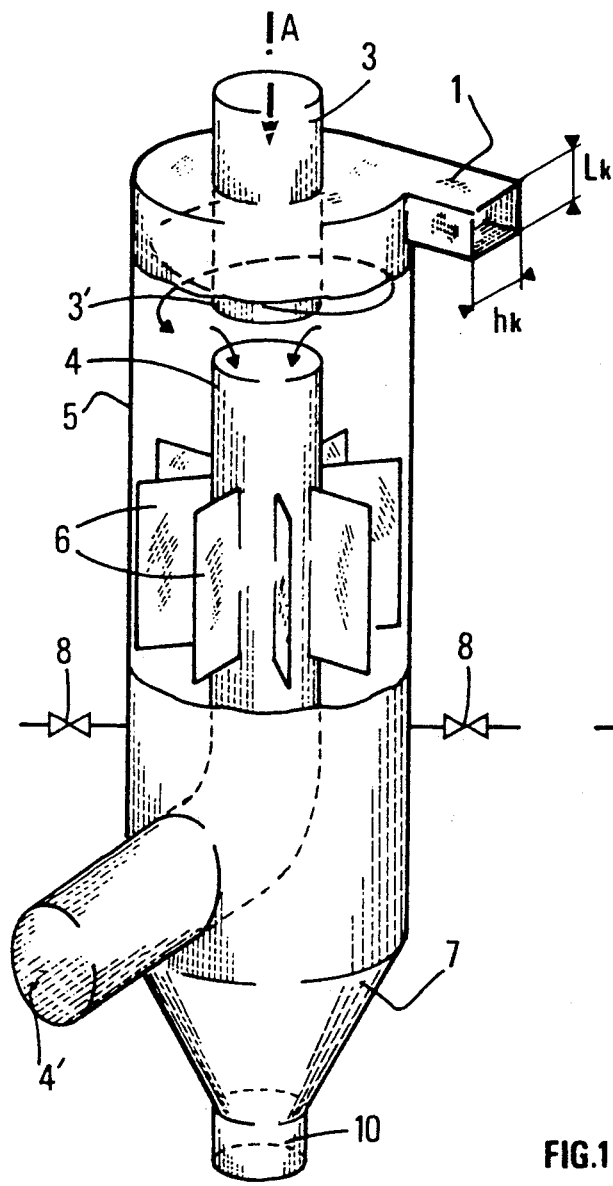
FIG. 2A is a perspective view of a cocurrent cyclone separator-mixer used in a preferred embodiment of the invention.
Figure 2B:
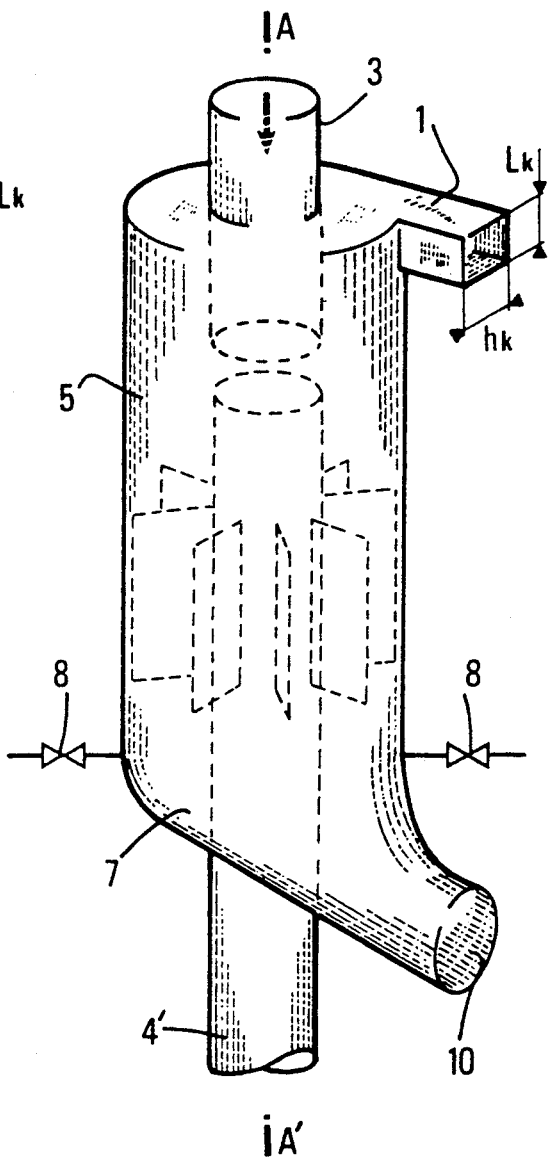
FIG. 2B is a perspective view of an apparatus used in the invention and which only differs from that of FIG. 2A by the discharge means (7) for the dense phase D1 introduced by the pipe (1), said means (7) making it possible in the embodiment shown in FIG. 2B for there to be a lateral discharge (10) of the dense phase D1 and in that shown in FIG. 2A an axial discharge (10) of the said phase.
Figure 1:
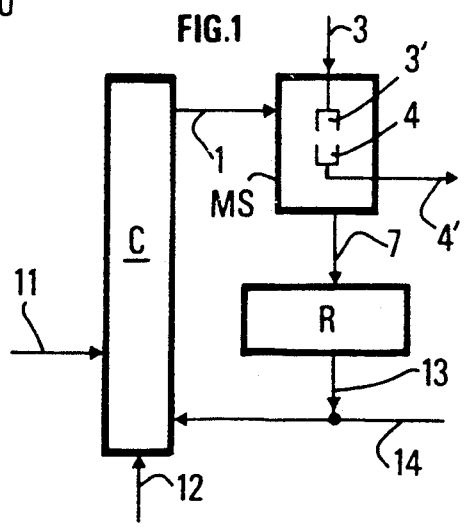
FIG. 1 diagrammatically shows a catalytic conversion apparatus according to the invention in which the conversion takes place in a reactor (C), into which the charge is introduced by the pipe (11), the solid particles comprising solid catalytic particles and forming the dense phase D1 being introduced by the pipe (14) and the solid entrainment gas by the pipe (12). The reactor is connected by a pipe (1) to a cocurrent cyclone separator-mixer (MS) making it possible to separate a solid phase from a gaseous phase, the latter containing the conversion products and is recovered by the pipe (4'), while carrying out the quenching of said gaseous phase by a product M2 in liquid, gaseous and/or solid form introduced by the pipe (3) and which circulates in a first internal enclosure up to the outlet (3') and then enters by the intake (4) into a second internal enclosure, where it circulates up to the outlet (4'). The dense phase D1 is supplied by the pipe (7) to a regenerator (R), in which the catalytic particles are at least partly regenerated before being returned, by the pipe 13 connected to the pipe (14), to the reactor (C). The mixture of the gaseous phase containing the conversion products and the product M2 is fed to a separator, where separation takes place of the product M2 from the gaseous phase and the product M2 is recycled to the separator-mixer (MS), optionally following cooling.
Figure 3:
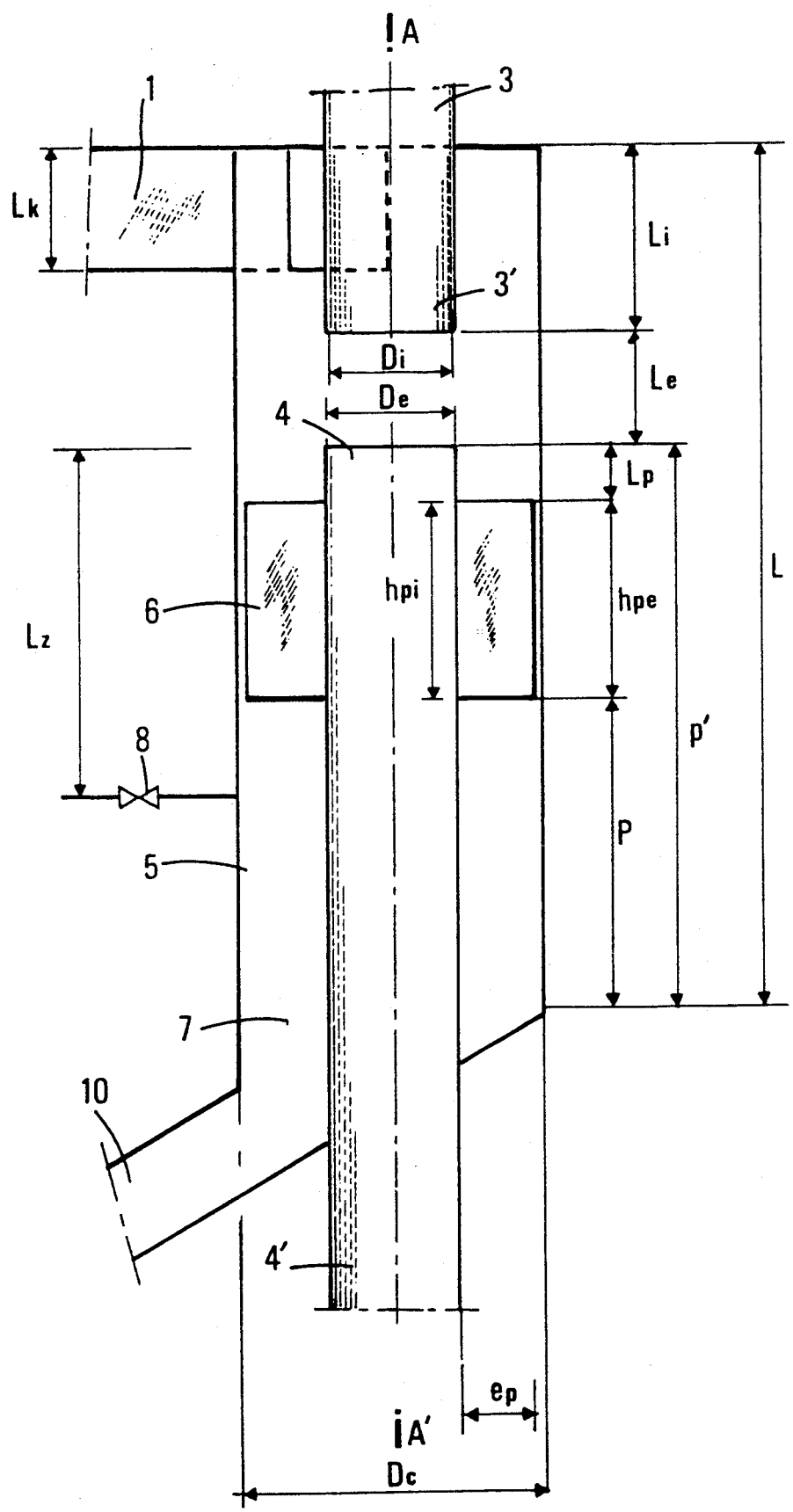
FIG. 3 is a sectional view of an apparatus used in the process of the invention and which is substantially identical to that shown in FIG. 2, having means (6) limiting the advance of the light phase L1 outside the internal enclosure.

The apparatuses used in the invention and diagrammatically shown in FIGS. 2A and 3 are elongated, substantially regular, along an axis (AA'), which is an axis of symmetry, comprise an external enclosure of diameter (Dc) see FIG. 3, bottom) and length (L) (see FIG. 3, right side) having a tangential intake (1), called the external intake and into which is introduced, in a direction substantially perpendicular to the apparatus axis, the mixture M1 containing at least one dense phase D1 and at least one light phase L1. This tangential intake preferably has a rectangular or square cross-section, whose side parallel to the apparatus axis has a size (Lk) (see FIG. 2B) normally approximately 0.25 to approximately once the diameter (Dc) and the side perpendicular to the apparatus axis has a size (hk) see FIGS. 2A and 2B normally approximately 0.05 to approximately 0.5 times the diameter (Dc).

The thus introduced mixture M1 passes around a first internal enclosure, positioned coaxially with respect to the external enclosure, having an axial intake (3), called the first internal intake, permitting the introduction of a light phase L2 or a dense phase D2 or preferably a mixture M2 containing a dense phase D2 and a light phase L2. This light phase L2 or dense phase D2 or mixture M2 circulates parallel to the apparatus axis (AA') up to the first internal outlet (3') having an internal diameter (Di) smaller than the diameter (Dc) of the external enclosure and which is normally approximately 0.05 to approximately 0.9 times said diameter (Dc) and preferably approximately 0.4 to approximately 0.8 times said diameter (Dc). The length (Li) between the extreme level of the tangential intake (1) and the first internal outlet is smaller than (L) and is normally approximately 0.2 to approximately 9.5 times the diameter (Dc) and preferably approximately 1 to approximately 3 times said diameter (Dc).

Although not shown in FIGS. 2A, 2B and 3, it is possible and usually desirable, in the case of high flow rates of the different phases at the apparatus intakes, to make use of means making it possible to favour the formation of the vortex, such as e.g. a helical roof or top dropping from the extreme level of the tangential intake (1) or an e.g. external helix, making it possible to limit the turbulence at the tangential intake (1). Normally the helical pitch is approximately 0.01 to approximately 3 times the value of (Lk) and usually approximately 0.5 to approximately 1.5 times said value.

The light phase L2 or the dense phase D2 or the mixture M2 then at least partly enters the second internal enclosure arranged coaxially with respect to the first internal enclosure, by a second internal intake (4) located at a distance (Le) from the first internal outlet (3'), said distance being preferably approximately 0.2 to approximately twice the diameter (Dc). The second enclosure is also entered by at least part of the light phase L1. This second internal intake (4) has an internal diameter (De) equal to or greater than (Di) and smaller than (Dc) and normally approximately 0.2 to approximately 0.9 times the diameter (Dc). This diameter (De) is preferably approximately 0.4 to approximately 0.8 times the diameter (Dc). By means of the second internal intake (4') of the apparatus is collected a mixture incorporating at least part of the light phase L1 and at least part of the light phase L2 or the dense phase D2 or the mixture M2 including a dense phase D2 and a light phase L2.

In accordance with the embodiment shown in FIGS. 2A and 3 the apparatus has, downstream in the flow direction of the two phases with respect to the second internal intake, at least one means (6) limiting the advance of the light phase L1 into the space between the inner wall of the external enclosure and the outer wall of the second internal enclosure or the external outlet (5). Said means (6) are preferably substantially planar blades, whose plane comprises the axis of the apparatus. These means (6) are normally fixed to at least one wall of one of the internal or external enclosures. These means (6) are preferably fixed to the outer wall of the second internal enclosure, in such a way that the distance (Lp) between the second internal intake and the point of said blades closest to said second internal intake is approximately 0 to approximately 5 times the diameter (Dc) and preferably approximately 0.1 to approximately once the said diameter (Dc).

The number of blades varies as a function of the residence time distribution accepted for the phase L1 and also a function of the external enclosure diameter (Dc). If the residence time of the phase L1 must have a wide distribution it will not be indispensable to have blades. The number of blades is normally between 0 and approximately 50 and usually, when the blades are present, at least 2 and e.g. 2 to approximately 50 and preferably 3 to approximately 50. By a limitation of the continuation of the vortex over the entire section of the cyclone, around the internal outlet (4) of the light phase, said blades permit a reduction and a control of the residence time distribution and consequently limit the deterioration of the products contained in the light phase circulating around the internal outlet.

Each of the blades normally has a size or width (ep) measured in the direction perpendicular to the apparatus axis and defined relative to the internal diameter (Dc) of the external enclosure or to the external diameter (D'e) of the second internal enclosure of approximately 0.01 to once the value $[((Dc)-(D'e))/2)]$ of the half-difference of said diameters (Dc) and (D'e), preferably approximately 0.5 to once said value and usually approximately 0.9 to once said value. In the case of a vertical apparatus used in the process of the invention, such as e.g. that shown in FIG. 2A and which has a lateral internal outlet (4') and when the blades are positioned after said internal outlet, said dimension (ep) can be approximately 0.01 to approximately once the value (Dc)/2 of the half-diameter of the external enclosure.

These blades have in each case on their edge closest to the axis of the internal enclosures in a direction parallel to said axis, an internal height or dimension (hpi) measured in the direction of the axis of the apparatus on the edge of said blade closest to the axis of the internal enclosures and an external height or dimension (hpe) measured in the direction of the axis of the apparatus on the edge of said blade closest to the internal wall of the external enclosure. These dimensions (hpi) and (hpe) normally exceed 0.1 times the diameter (Dc) and are e.g. approximately 0.1 times to approximately 10 times the diameter (Dc) and most usually 1 to approximately 4 times said diameter (Dc). Preferably each of these blades have a dimension (hpi) equal to or greater than their dimension (hpe).

According to the embodiment shown in FIGS. 2A and 3 the apparatus has, downstream in the flow direction of the different phases with respect to the second internal intake, at least one means (8) permitting the possible introduction of a light phase L3 at at least one point located between the second internal intake (4) of the second internal enclosure and the external outlet (10) of the dense phase D1. Said point or points are preferably at a distance (Lz) from the second internal enclosure intake (4). The distance (Lz) preferably has a value at least equal to the sum of the values of (Lp) and (hpi) and at the most to the distance between the second internal enclosure intake (4) and the discharge means (7) for the dense phase D1. Said light phase L3 can e.g. be introduced in the case where it is desirable to carry out the stripping of the dense phase D1. The light phase L3 is preferably introduced at several points, which are normally symmetrically distributed in a plane at whose level the introduction takes place around the external enclosure.

The introduction point or points of said light phase L3 are normally at a distance at least equal to 0.1 times the diameter (Dc) of the second internal enclosure intake (4), when the apparatus has no means (6) or the point of said means (6) closest to the discharge means (7) for the dense phase D1, when the apparatus has such means (6). The introduction point or points of the light phase L3 are preferably located in the vicinity of the external outlet (10) and usually in the vicinity of the discharge means (7) for the dense phase D1.

The dimension (p') between the level of the second internal intake (4) and the discharge means (7) for the dense phase D1 is determined on the basis of the other dimensions of the various means forming the apparatus and the external enclosure length (L) measured between the extreme level of the tangential intake (1) and the discharge means (7) for the dense phase D1. This dimension (L) is normally approximately 1 to approximately 35 times the external enclosure diameter (Dc) and usually approximately 1 to 25 times said diameter (Dc). It is in the same way possible to calculate the dimension (P) between the point of means (6) closest to the discharge means (7) for the dense phase D1 and the said means (7), on the basis of the other dimensions of the various means forming the apparatus and the length (L).

It would not pass outside the scope of the present invention for the apparatus axis (AA') to form an angle with the vertical. However, it is preferable in this case, when use is made of the means (6) limiting the circulation of the light phase L1 into the external outlet (5) and therefore reducing the residence time distribution of said phase L1 in the apparatus, to position them vertically and therefore obtain an apparatus having, in the case of an axial internal outlet (4'), a bend or elbow beyond which the said means (6) will be positioned in the vertical external outlet. In the same way in the case of an apparatus as shown in FIG. 2A having a lateral outlet (4'), it is possible to position the means (6) limiting the circulation of the light phase L1 in the external outlet (5) and therefore reducing the residence time distribution of said phase L1 in the apparatus downstream of the level of the internal level (4') and upstream of the means (7).

The means (6) limit the progression of the vortex of the light phase L1 in the external outlet (5). The position and number of the said means (6) consequently influence the performance characteristics of the separation of the phases D1 and L1 contained in the mixture M1 (pressure drop and efficiency of the collection of the dense phase D1) and also influence the penetration of the vortex of the light phase L1 into the outlet (5). Therefore these parameters will be carefully chosen as a function of the desired results and the acceptable pressure drop. In particular, the number of blades, their shape and their position will be carefully chosen taking account of their influence on the flow of the solid D1, in conjunction with the sought limitation of the advance of the vortex into the external outlet (5).

Figure 4:
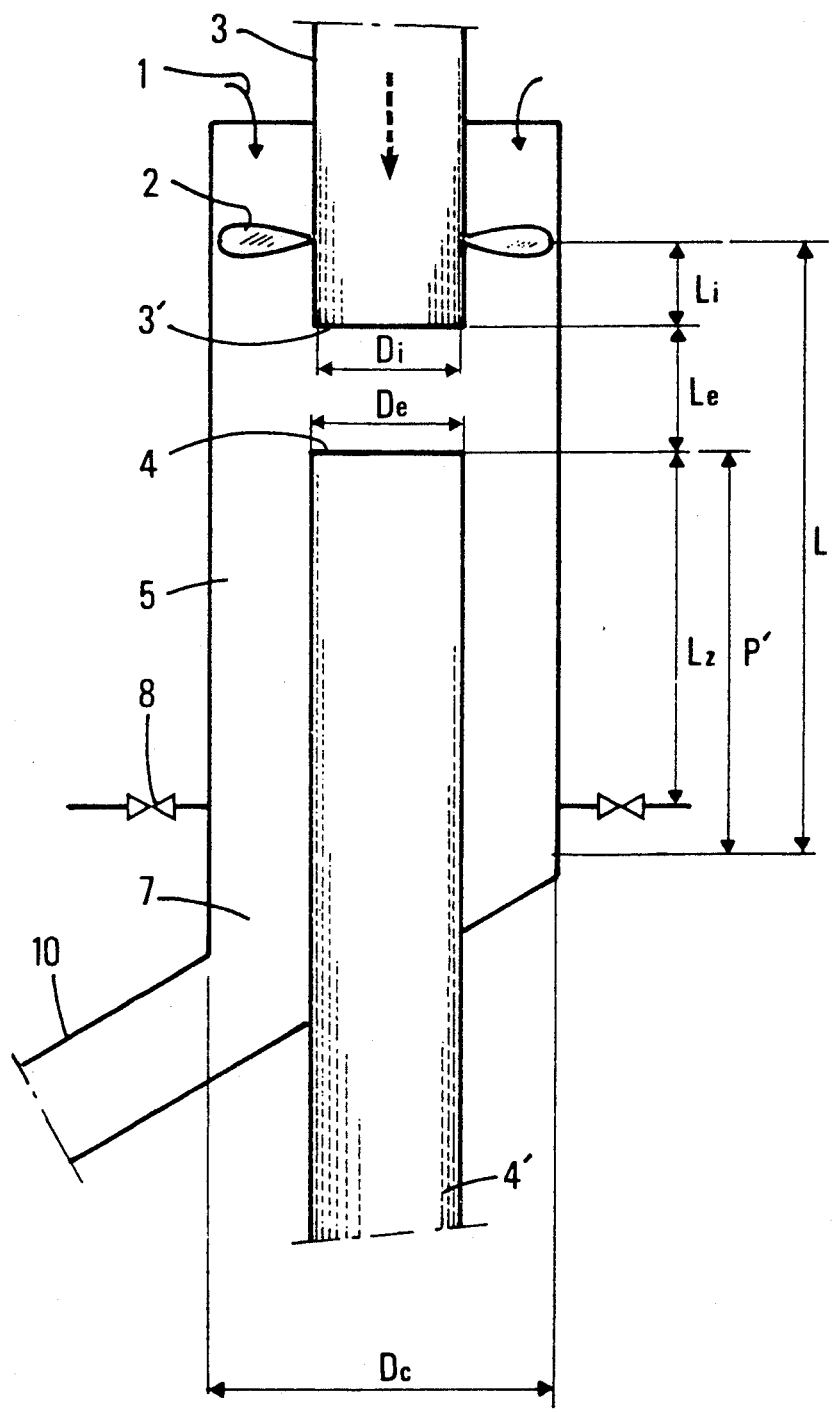
FIG. 4 is a perspective view of an apparatus in accordance with the invention.

In FIG. 4, the perspective view is of an appropriate according to the invention having an external enclosure of diameter (Dc) with an intake (1), called the external axial intake, into which is introduced in a direction substantially parallel to the apparatus axis (AA'), the mixture M1 containing a dense phase D1 and a light phase L1. The said apparatus also has means (2) placed inside the intake (1) in the space between the inner wall of the external enclosure and the outer wall of the first internal enclosure making it possible to give downstream, in the flow direction of said mixture M1, a helical or whirling movement at least to the phase L1 of said mixture M1. These means are normally inclined blades. The apparatus length L is measured between the means making it possible to create a vortex, at least on the phase L1, and the discharge means (7) for the dense phase D1. The said apparatus has no means (6) for limiting the penetration of the vortex into the external outlet (5). All the other characteristics are identical to those described in conjunction with the apparatus as shown in FIGS. 2A and 3, particularly the dimensions are those given hereinbefore. The variants described in conjunction with the apparatuses shown in FIGS. 2A and 3 are also possible to envisage a lateral internal outlet (4') and an axial external outlet (10), as in the embodiment of FIG. 2A as well as the use of means (6) in the external outlet (5). The discharge means (7) for the dense phase D1 normally make it possible to collect and pipe said phase D1 up to the external outlet (10).

These means are normally constituted by an inclined base or a cone axed or not on the internal outlet (4').

The apparatuses of the present invention shown in the drawings have a single axis (AA'), but it would not pass outside the scope of the invention if the apparatus was constructed with several axes e.g. forming an angle between them. In this case the axis (AA') would be the axis of that part of the apparatus located between the first internal intake (3) and the first internal outlet (3') and the value of the diameter (Dc) would be that measured at said internal outlet (3'). Here again the axis (AA') would be the axis of the second internal enclosure, the two internal enclosures remaining in a coaxial position (such a case is e.g. that of an apparatus having a bent external enclosure).

The apparatus diameter (Dc) measured at the first internal outlet (3') is normally approximately 0.01 to approximately 10 m and most usually approximately 0.05 to approximately 2m. It is normally preferable to maintain a constant diameter over the entire apparatus length (L) or even from the injection level of the mixture M1 up to the level of the means (7) for the discharge of the dense phase D1. However, it would not pass outside the scope of the invention to have an apparatus with cross-sectional widenings or narrowings between the said levels.

In order to obtain a good separation of the phase L1 contained in the mixture M1 and also incorporating the phase D1 and an effective mixing of said phase L1 with a phase L2 or with a phase D2 or with a mixture M2 of said phases L2 and D2, it is preferable to have a high surface velocity for the entry of said phase L1. This velocity will e.g. be approximately 0.1 to approximately 250 m×s$^{-1}$ Nmeters per second) and preferably approximately 0.5 to approximately 75 m×s$^{-1}$ and most frequently approximately 1 to approximately 20 m×s$^{-1}$. The weight ratio of the flow rate of phase D1 to the flow rate of the phase L1 is normally approximately 2:1 to approximately 100:1 and most frequently approximately 5:1 to approximately 50:1. The flow rate of the phase L2 or the phase D2 or the mixture M2 normally represents by weight approximately 0.1 to approximately 1000% of the flow rate of the phase D1 and most frequently approximately 10 to approximately 300% of the flow rate of phase D1. The surface velocity V2 of the phase L2, when it is present alone or within the mixture M2, is normally approximately 1 to approximately 500% of the mean axial velocity V1 over the entire section of diameter (Dc) located between the first internal outlet (3') and the second internal intake (4) defined by the relation:

$$V1 = L1/(\pi \times Dc^2/4)$$

in which L1 is expressed in m$^3$×s$^{-1}$ (cubic meters per second) and Dc in m. The surface velocity V2 is preferably approximately 5 to approximately 150% of the velocity V1.

It is e.g. possible by increasing the pressure downstream, in the flow direction of the light phase L2 or the dense phase D2 or the mixture M2, of the second internal intake (4) or by reducing the pressure downstream, in the flow direction of the dense phase D1, of the discharge means (7) for said phase, to draw off a varying amount of the phase L1 with the phase D1 and simultaneously obtain at the second outlet (4') a mixture substantially completely free from the phase D1. Usually withdrawal takes place of approximately 1 to approximately 10% of the phase L1 with the phase D1. The pressure variations making it possible to act on the quantity of the phase L1 drawn off with the phase D1 are ensured by known means and which e.g. act on the temperature of the quenching by modifying the flow rates of the phases L2 or D2 or the mixture M2, or by modifying the flow rate of phase L3, or by modifying the operating conditions downstream of the outlet (10).

In the various apparatuses used in the present invention and in the different injection procedures for the mixture M1, such a drawing off makes it possible to improve the recovery efficiency for the dense phase D1. Thus, an advantageous embodiment of the apparatus will comprise at least one means permitting the drawing off, through the external outlet, of at least part of the light phase L1 mixed with the dense phase D1. The choice between an apparatus having a tangential intake for the mixture M1 and an apparatus having an axial intake for the mixture M1 is normally guided by the weight ratio of the flow rates of the phases L1 and D1. When this ratio is below 5:1, it can be advantageous to choose an apparatus with an axial intake.

The present invention also relates to an apparatus for the entrained bed catalytic conversion of a charge containing at least one oxygen compound into olefinic hydrocarbons rich in compounds having 2 to 4 carbon atoms in their molecule, having an elongated enclosure, in which the said conversion is performed under appropriate conditions and comprising, in the vicinity of a first end, from upstream to downstream in the charge displacement direction, at least one means for introducing at least one entrainment fluid, at least one means for introducing at least one solid forming a dense phase D1 containing catalytic particles, at least one means for introducing the said charge, the apparatus comprising in the vicinity of a second end of said enclosure at least one means, connected to said enclosure, for separating from their mixture M1 solid particles and gases forming a light phase L1 and the quenching of said gases containing the products of the at least partial conversion of said charge and at least one means for regenerating at least part of the catalytic solid particles connected on the one hand to the said separation and quenching means and on the other to the said enclosure in the vicinity of said first end, so as to permit the at least partial regeneration of the solid catalytic particles and the recycling of said solid particles in said enclosure, characterized in that the means for separating the solid particles and for quenching the gases is a cocurrent cyclone separator-mixer comprising in combination:

at least one external enclosure, extended along at least one axis, having a substantially circular cross-section of diameter (Dc) and length (L), having in the vicinity of a first end at least one introduction means permitting the introduction, by an intake (1) called the external intake, of the mixture M1 containing the dense phase D1 and the light phase L1, said means being able to give at least to the phase L1 a helical movement in the flow direction of said mixture M1 into the external enclosure and also having means for separating the phases D1 and L1 and, in the vicinity of a second end opposite to the first end, recovery means making it possible to recover by an outlet (7), called the external outlet, at least part of the dense phase D1, at least one first internal enclosure, extended along at least one axis, having a substantially circular cross-section and having a length (Li) smaller than (L) and arranged coaxially with respect to said external enclosure, having an intake (3), called the first internal intake, located in the vicinity of the external intake of the external enclosure, at least one introduction means making it possible to introduce by said first internal intake a light phase L2 or a dense phase D2 or a mixture M2 incorporating both a light phase L2 and a dense phase D2, said phases L2 or D2 or said mixture M2 having a temperature below the temperature of the phase L1, said means making it possible to introduce said phase L2 or D2 or said mixture M2 in such a way that their flow takes place in the same direction as the flow of the mixture M1 up to a first internal outlet (3') having an internal diameter (Di) smaller than (Dc), opposite to said first internal intake (3), by which said phase L2 or said phase D2 or said mixture M2 leaves by the said outlet (3') the first internal enclosure, at least one second internal enclosure, extended along at least one axis, having a substantially circular cross-section and positioned coaxially with respect to the first internal enclosure and having a first end located at a distance (Le) from the first internal inlet (3') of the first internal enclosure, said distance (Le) being such that the sum of the distances (Le) and (Li) is at the most equal to (L) and which is entered, via an intake (4), called the second internal intake, of internal diameter (De) equal to or larger than (Di) and smaller than (Dc), at least part of the light phase L1 and at least part of the light phase L2 or the dense phase D2 or the mixture M2, said second internal enclosure having an outlet (4'), called the second internal outlet, located in the vicinity of the external outlet (7) of the external enclosure, at least one discharge means permitting the discharge by said second internal outlet of a mixture M3 comprising at least part of the light phase L1 and at least part of the light phase L2 or the dense phase D2 or the mixture M2 and at least one means making it possible to separate and recover from said mixture M3 on the one hand the said phase L2 or the said phase D2 or the said mixture M2 and on the other the cooled phase L1 containing the olefinic hydrocarbons formed during the conversion.

Within the scope of the present invention no mention is made of the solids and catalysts used, or of the various fluids used, which are of a conventional nature in connection with the catalytic conversion of oxygen compounds into olefinic hydrocarbons. The entrainment fluid is most usually chosen from within the group formed by steam, inert gases or gaseous hydrocarbons, or mixtures of these compounds. The reaction performance conditions usually involve working in an entrained fluid bed. In this case the fluidization fluid is usually the same as the entrainment fluid. This single fluid is then subdivided into two fractions, one forming the fluidization fluid and the other the entrainment fluid. The catalysts used are preferably zeolytic catalysts.

The operating conditions relative to the conversion processes for the oxygen-containing charges such as methanol are e.g. described in the following patents: U.S. Pat. Nos. 4,689,205, 3,969,426 and 4,229,608, but none of these patents described the use of a cocurrent cyclone separator for improving the speed of the solid-gas separation.

The operating conditions for the conversion of the oxygen-containing charge are generally as follows:

the charge, which usually contains an alcohol, normally methanol, generally contains 50 to 100, preferably 70 to 90% by weight of oxygen compounds and 0 to 50, preferably 5 to 30% by weight water. The charge can also contain an inert gas, such as e.g. nitrogen alone or mixed with steam in the proportion indicated hereinbefore for the steam. In the most frequent case where the charge contains methanol, it can be constituted by crude methanol such as e.g. that coming from a unit for synthesizing this compound from a gas containing carbon monoxide, the injection temperature is usually equal to the dew point of the charge, the absolute pressure in the conversion unit is normally 0.1 to 0.5 megapascal (MPa) and is usually approximately 0.2 MPa, the reaction zone temperature is usually 500° to 620° C. and most frequently 550° to 590° C., the residence time in the reaction zone is normally 0.05 to 10 seconds and most frequently 0.5 to 3 seconds, the velocity of the gases in the reaction zone is normally 0.5 to 40 m/s and most frequently 1 to 20 m/s, the velocity of the solids in the reaction zone is normally close to that of the gases and is generally 0.5 to 40 m/s and most frequently 1 to 20 m/s.

In a preferred embodiment of the invention the charge incorporates at least one alcohol, preferably methanol and is introduced in the gaseous state.

The operating conditions are chosen so that the composition of the products obtained, expressed by the carbon yield in ethylene compounds having 2 to 4 carbon atoms in their molecule, exceeds 70% and preferably 80%. The products obtained can be particularly rich in ethylene (carbon yield for the ethylene exceeding 40%) or particularly rich in propylene (carbon yield for the propylene exceeding 60%).

The density of the solids in the reactor is usually 10 to 700 kg/m$^3$ and most usually 20 to 400 kg/m$^3$.

The C/O ratio of the catalyst to the charge mass flow rate is normally approximately 2:1 to approximately 50:1 and most frequently 5:1 to approximately 30:1.

We claim:

1. A process for catalytic conversion of a charge comprising at least one oxygen compound, into olefinic hydrocarbons rich in compounds having 2 to 4 carbon atoms per molecule, said process employing entrained bed conversion of said charge, in an elongated conversion reaction zone, under appropriate conditions and in the presence of a catalyst in the form of solid particles, said process comprising:

(a) supplying to a zone proximate a first end of said reaction zone at least one dense phase D1 of solid particles containing catalytic particles, (b) supplying in the zone proximate the first end of said reaction zone at least one entrainment fluid, (c) introducing the charge as a gas or atomized liquid downstream of said zone in step (a), (d) contacting said solid particles and said charge in the zone proximate said first end, (e) circulating the solid particles and the charge in said elongated conversion reaction zone so as to convert said charge to product gases comprising olefinic hydrocarbons and at least partly deactivate the catalytic solid particles by depositing coke thereon, (f) separating from the product gases in step (e) a dense phase D1 and a light phase L1, and quenching the light phase in a quenching zone proximate a second end of the conversion zone opposite said first end, (g) regenerating in at least one regenerating zone at least a portion of the at least partly deactivated solid catalytic particles containing the dense phase D1, and (h) recycling said dense phase containing at least partly regenerated solid catalytic particles into a recycling zone proximate said first end, wherein, the dense phase D1 is separated from the light phase L1 containing the conversion products and said light phase is quenched in a separation and quenching said process takes place in an apparatus comprising:

(i) an external enclosure, extended along at least one axis, having a substantially circular cross-section of diameter (Dc) and length (L), into which is introduced in the first end of said external enclosure by an external intake (1) a mixture M1 from step (e) comprising a dense phase D1 and a light phase L1 containing product gases, which is circulated from said first end to a second end opposite to the first end of said external enclosure, while subjecting at least the phase L1 of said mixture to a helical movement in the direction of flow of said mixture M1, the dense phase D1 being separated from the light phase L1, by means of an external outlet (7), and recovering at least part of the dense phase D1 and passing the light phase L1 into a second internal intake (4), of a second internal enclosure;

(ii) a first internal enclosure, extended along at least one axis and having a substantially circular cross-section, which has a length (Li) smaller than (L) and arranged coaxially relative to said external enclosure, into which is introduced by a first internal intake (3), a light phase L2 or a dense mixture D2 or a mixture M2 comprising both the light phase L2 and a dense phase D2, said phase L2 or D2 or said mixture M2 having a temperature which is lower than the temperature of the phase L1, the said phase L2 or D2 or said mixture M2 being circulated from said first internal intake to a first internal outlet (3'), which has an internal diameter (Di) smaller than (Dc), which is opposite to said first internal intake (3), by which the said phase L3 or the said phase D2 or the said mixture M2 leaves said first internal enclosure by said outlet (3');

(iii) a second internal enclosure extended along at least one axis having a substantially circular cross-section and positioned coaxially relative to said first internal enclosure, into which penetrates a second internal intake (4) having an internal diameter (De) equal to or larger than (Di) and smaller than (Dc), said second internal intake being located at a distance (Le) from the first internal outlet (3') of the first internal enclosure, said distance (Le) being such that the sum of the distances (Le) and (Li) is at most equal to (L), at least part of the light phase L1 and at least part of the light phase L2 or the dense phase D2 or the mixture M2 from said second enclosure is discharged by a second internal outlet (4'), which is opposite to said second internal intake; and (iv) a zone into which is passed a mixture M3 comprising at least part of the light phase L1 and at least part of the light phase L2 or the dense phase D2 or the mixture M2 and in which separation and recovery takes place of said phase L2 or said phase D2 or said mixture M2 and of the cooled phase L1 containing the olefinic hydrocarbons formed during the conversion.

2. A process according to claim 1, wherein the distance (Le), between the first internal outlet (3') of the first internal enclosure and the first internal inlet (4) of the second internal enclosure, is approximately $0.1 \times (Dc)$ to approximately $10 \times (Dc)$.

3. A process according to claim 1, wherein the mixture M1 is introduced into the separation and quenching zone in a direction substantially perpendicular to the axis of its external enclosure, or in a direction substantially parallel to the axis of said external enclosure.

4. A process according to claim 1, wherein the separation and quenching zone comprises, in the space located between the outer wall of the second internal enclosure and the inner wall of the external enclosure, downstream of the second internal intake, at least one means for retarding the flow of the light phase L1.

5. A process according to claim 4, wherein the means for retarding the flow of the light phase L1 in the space between the outer wall of the second internal enclosure and the inner wall of the external enclosure comprises substantially planar blades, whose plane includes the axis of said external enclosure.

6. A process according to claim 5, wherein the separation and quenching zone has 2 to approximately 50 blades fixed to the outer wall of the second internal enclosure, so that the distance between the second internal intake and the point of said blades closest to said second internal intake is approximately 0 to approximately $5 \times (Dc)$.

7. A process according to claim 5, wherein each blade has a dimension (ep), measured in the direction perpendicular to the axis of the external enclosure of said separation and quenching zone, of approximately 0.01 to approximately 1 times the value $[((Dc)-(D'e))/2]$ corresponding to the distance between the outer wall of the second internal enclosure of external diameter (D'e) and the internal wall of the external enclosure of internal diameter (Dc), a dimension (hpi), measured on the edge of the blade closes to the axis of the internal enclosures in the direction parallel to said axis, and a dimension (hpe), measured in the direction parallel to the axis of the external enclosure of said separation and quenching zone on the edge of the blade closest to the internal wall of the external enclosure, said dimensions (hpi) and (hpe) being approximately $0.1 \times (Dc)$ to approximately $10 \times (Dc)$.

8. Process according to claim 7, wherein each blade has a dimension (hpi) equal to or greater than (hpe).

9. A process according to claim 1, wherein a fluid (L3) is introduced into the separation and quenching zone whereby the solid particles are strippped from the dense phase D1.

10. A process according to claim 1 wherein the charge comprises at least one alcohol, and is introduced in the gaseous state.

11. In a process for the catalytic conversion of a charge of at least one oxygen compound into olefinic hydrocarbons having 2-4 carbon atoms, comprising contacting a dense phase containing solid catalyst particles and an entrainment fluid with said charge, and recovering an effluent comprising a light phase containing products and entrainment fluid, and a dense phase containing deactivated catalyst, the improvement wherein the dense phase is separated from the light phase containing products and said light phase is quenched, said separation and queching being simultaneously effected in a cyclone separator.

* * * * *